(12) United States Patent
Tian et al.

(10) Patent No.: US 6,597,932 B2
(45) Date of Patent: Jul. 22, 2003

(54) GENERATION OF SPATIALLY-AVERAGED EXCITATION-EMISSION MAP IN HETEROGENEOUS TISSUE

(75) Inventors: Wei Dong Tian, West Roxbury, MA (US); Pierre Trepagnier, Medford, MA (US)

(73) Assignee: Argose, Inc., Waltham, MA (US)

( * ) Notice: Subject to any disclaimer, the term of this patent is extended or adjusted under 35 U.S.C. 154(b) by 7 days.

(21) Appl. No.: 09/785,549

(22) Filed: Feb. 20, 2001

(65) Prior Publication Data

US 2001/0046045 A1 Nov. 29, 2001

Related U.S. Application Data

(60) Provisional application No. 60/183,345, filed on Feb. 18, 2000.

(51) Int. Cl.$^7$ .............................. A61B 5/00; A61B 6/00; G01N 21/64

(52) U.S. Cl. ..................................................... 600/317

(58) Field of Search ................................. 600/317, 476, 600/477, 478; 356/317, 311, 318; 250/459.1

(56) References Cited

U.S. PATENT DOCUMENTS

| | | | |
|---|---|---|---|
| 3,652,855 A | * 3/1972 | McIntyre et al. | 250/459.1 |
| 5,106,387 A | * 4/1992 | Kittrell et al. | 600/477 |
| 5,303,026 A | 4/1994 | Strobl et al. | 356/318 |
| 5,345,941 A | 9/1994 | Rava et al. | |
| 5,491,344 A | * 2/1996 | Kenny et al. | 250/461.1 |
| 5,569,591 A | 10/1996 | Kell et al. | 435/29 |
| 5,579,773 A | * 12/1996 | Vo-Dinh et al. | 600/317 |
| 5,601,079 A | 2/1997 | Wong et al. | 128/633 |
| 5,676,143 A | 10/1997 | Simonsen et al. | 128/633 |
| 5,725,480 A | 3/1998 | Oosta et al. | 600/310 |
| 5,865,754 A | * 2/1999 | Sevick-Muraca et al. | 600/476 |
| 5,876,339 A | * 3/1999 | Lemire | 600/476 |
| 6,024,978 A | 2/2000 | Hauer et al. | 424/450 |
| 6,044,285 A | 3/2000 | Chaiken et al. | 600/316 |
| 6,049,727 A | 4/2000 | Crothall | 600/310 |
| 6,078,828 A | 6/2000 | Yasuda et al. | 600/310 |
| 6,095,982 A | * 8/2000 | Richards-Kortum et al. | 600/476 |

(List continued on next page.)

FOREIGN PATENT DOCUMENTS

| | | | |
|---|---|---|---|
| EP | 0063431 | 10/1982 | G01N/21/31 |
| EP | 0623307 | 11/1994 | A61B/5/00 |
| GB | 2300045 | 10/1986 | A61B/5/00 |
| WO | WO92/15008 | 9/1992 | G01N/21/65 |
| WO | WO94/10901 | 5/1994 | A61B/5/00 |
| WO | WO95/06431 | 3/1995 | A61B/5/00 |
| WO | WO96/07889 | 3/1996 | G01N/21/64 |
| WO | WO/9748331 | 12/1997 | |
| WO | WO 99/51142 | 10/1999 | |
| WO | WO/9957529 | 11/1999 | |

OTHER PUBLICATIONS

JiJi, Renee D., et al.: "Excitation–emission matrix fluorescence based determination of carbamate pesticides and polycyclic aromatic hydrocarbons," Analytica Chimica Acta, vol. 397, 1999, pp. 61–72.

Primary Examiner—Joseph Pelham
(74) Attorney, Agent, or Firm—Mintz, Levin, Cohn, Ferris, Glovsky and Popeo, P.C.; Ivor R. Elrifi, Esq.; Christina V. Karnakis, Esq.

(57) ABSTRACT

An instrument for evaluating fluorescence of a heterogeneous tissue includes means for exciting a two-dimensional portion of the tissue surface with excitation radiation at a plurality of excitation wavelengths, means for collecting emission radiation from the two-dimensional portion of the tissue surface simultaneously with excitation of the portion, and means for forming a two-dimensional excitation-emission map of the excitation radiation and the simultaneously collected emission radiation and spatially averaging the excitation and emission radiation.

8 Claims, 2 Drawing Sheets

U.S. PATENT DOCUMENTS

| | | |
|---|---|---|
| 6,124,597 A | 9/2000 | Shehada et al. .......... 250/461.2 |
| 6,157,041 A | 12/2000 | Thomas et al. ............. 250/573 |
| 6,232,609 B1 | 5/2001 | Snyder et al. ........... 250/461.1 |
| 6,240,309 B1 * | 5/2001 | Yamashita et al. .......... 600/476 |
| 6,258,576 B1 | 7/2001 | Richards-Kortum et al. ......................... 435/172 |
| 6,309,884 B1 | 10/2001 | Cooper et al. ................. 436/14 |
| 6,370,422 B1 * | 4/2002 | Richards-Kortum et al. ......................... 600/478 |
| 6,377,842 B1 * | 4/2002 | Pogue et al. ................. 600/478 |
| 6,405,065 B1 | 6/2002 | Malin et al. ................. 600/310 |
| 6,505,059 B1 | 1/2003 | Kollias et al. .............. 600/316 |

* cited by examiner

Fiber Optic Head for 3-D Fluorescence Spectrometer

GENERATION OF SPATIALLY-AVERAGED EXCITATION-EMISSION MAP IN HETEROGENEOUS TISSUE

RELATED APPLICATION

The present invention claims priority to U.S. Provisional Patent Application No. 60/183,345, filed Feb. 18, 2000, and titled, "Generation of Spatially-Averaged Excitation-Emission Map in Heterogeneous Tissue."

BACKGROUND OF THE INVENTION

1. Field of the Invention

This invention relates to the rapid generation of in vivo tissue auto-fluorescence spectra, and in particular to methods and devices for the acquisition of two-dimensional fluorescence excitation-emission maps, useful in the evaluation of heterogeneous tissues.

2. Description of the Background

Tissue fluorescence has been used extensively for various medical purposes, including diagnosing disease, such as cancer of the cervix, assessment of skin aging, and monitoring tissue analytes.

A fluorescent species, i.e., fluorophore, will absorb incident light, and re-emit it at a longer wavelength. Therefore, unlike absorption spectroscopy, fluorescence spectra can only be completely characterized by studying the relationships between emission and excitation found on a two-dimensional excitation-emission map. However, due to conventional instrumentation constraints, excitation-emission maps have been sparingly used until recently. Instead, spectra taken from a projection onto either the excitation or emission axes, i.e., only varying the excitation or emission wavelengths, have been gathered. For example, emission scans, which involve excitation of the sample with a single wavelength and scanning the sample's emissions, have been popular because they can utilize a laser light source. Further, excitation scans require generating illumination over many wavelengths, and so are typically performed with a continuous-spectrum light source. However, because the spectrum is recorded at a constant emission wavelength, excitation scans require the use of sensitive photomultiplier detectors.

Both emission and excitation scans, as well as synchronous scans, in which both excitation and excitation wavelengths are simultaneously incremented, have been extensively described in the literature. In addition, for homogeneous samples prepared in a cuvette, at least one commercial manufacturer offers an instrument which gathers an excitation-emission map at once in a cuvette. It does this by spreading the excitation beam along the length of the cuvette. The fall spectrum excites any homogeneous sample. The resulting fluorescence is then collected and diffracted in the orthogonal direction. This process results in a two-dimensional excitation/emission image, which is collected with a two-dimensional CCD device.

This instrument depends upon sample homogeneity to work. However, in vivo tissues are quite inhomogeneous, and so would not be suitable for use with this instrument (even if taken ex vivo and placed in a cuvette). In fact, this inhomogeneity is a problem with in vivo fluorescence, as many spectra at different sites must be obtained and averaged in order to get a representative spectrum.

Consequently, there is a need for a device that can be used to gather and process fluorescent spectra from tissue in vivo, despite any inhomogeneity which may be present in the tissue.

SUMMARY OF THE INVENTION

The present invention overcomes the problems and disadvantages associated with current strategies and designs and provides a device useful for analyzing heterogeneous tissues in vivo. The present invention applies the technique of gathering an excitation-emission map simultaneously, using a two-dimensional CCD or similar photon detector, to in vivo tissue, while at the same time ameliorating the inhomogeneity problem that plagues in vivo fluorescence spectroscopy.

Accordingly, one embodiment of the invention is directed to a method for evaluating fluorescence of a heterogeneous tissue comprising the steps of exciting a two-dimensional portion of the tissue surface with excitation radiation at a plurality of excitation wavelengths, collecting emission radiation from the two-dimensional portion of the tissue surface simultaneously with excitation, and forming a two-dimensional excitation-emission map of the excitation radiation and the simultaneously collected emission radiation and spatially averaging the excitation and emission radiation.

Another embodiment is directed to an instrument for evaluating fluorescence of a heterogeneous tissue comprising means for exciting a two-dimensional portion of the tissue surface with excitation radiation at a plurality of excitation wavelengths, means for collecting emission radiation from the two-dimensional portion of the tissue surface simultaneously with excitation, and means for forming a two-dimensional excitation-emission map of the excitation radiation and the simultaneously collected emission radiation and spatially averaging the excitation and emission radiation.

Another embodiment is directed to a method of rapidly gathering UV and visible fluorescence spectra in vivo which have been spatially averaged over tissue, the method comprising the steps of illuminating strips of tissue with excitation radiation simultaneously at a plurality of excitation wavelengths, collecting emission radiation simultaneously from the strips of tissue with the step of illuminating with the plurality of excitation wavelengths, and disposing the emission radiation onto a two-dimensional array of detector elements, wherein the two-dimensional detector disposition is arranged by wavelength to form a two-dimensional excitation-emission map, in which all elements in the map are collected at once.

Still another embodiment is directed to an instrument for rapidly gathering UV and visible fluorescence spectra in vivo which have been spatially averaged over tissue, the method comprising means for illuminating strips of tissue with excitation radiation simultaneously at a plurality of excitation wavelengths, means for collecting emission radiation simultaneously from the strips of tissue with the step of illuminating with the plurality of excitation wavelengths, and means for disposing the emission radiation onto a two-dimensional array of detector elements, wherein the two-dimensional detector disposition is arranged by wavelength to form a two-dimensional excitation-emission map, in which all elements in the map are collected at once.

Other embodiments and advantages of the invention are set forth in part in the description which follows, and in part, will be obvious from this description, or may be learned from the practice of the invention.

DESCRIPTION OF THE INVENTION

As embodied and broadly described herein, the present invention is directed to methods and devices for the acquisition of two-dimensional fluorescence excitation-emission maps, useful in the evaluation of non-homogenous tissues.

The present invention applies the technique of gathering an excitation-emission map simultaneously, using a two-dimensional CCD or similar photon detector, to in vivo tissue, while at the same time ameliorating the inhomogeneity problem that plagues in vivo fluorescence spectroscopy.

An important feature of the present invention is the spatial averaging of the excitation and emission radiation. In contrast to the prior art, in which excitation was spread into a line so that each spectral region illuminated only a very small sample patch, in the present invention a substantial strip or area of tissue is illuminated, thus spatially averaging over the sample.

In a preferred embodiment, this function is performed with a large fiber bundle, so that no moving parts are present. In alternate, less-preferred embodiments, the strip may be generated over time by sequentially scanning, using a moving mirror or other beam steering device.

Figure 1:
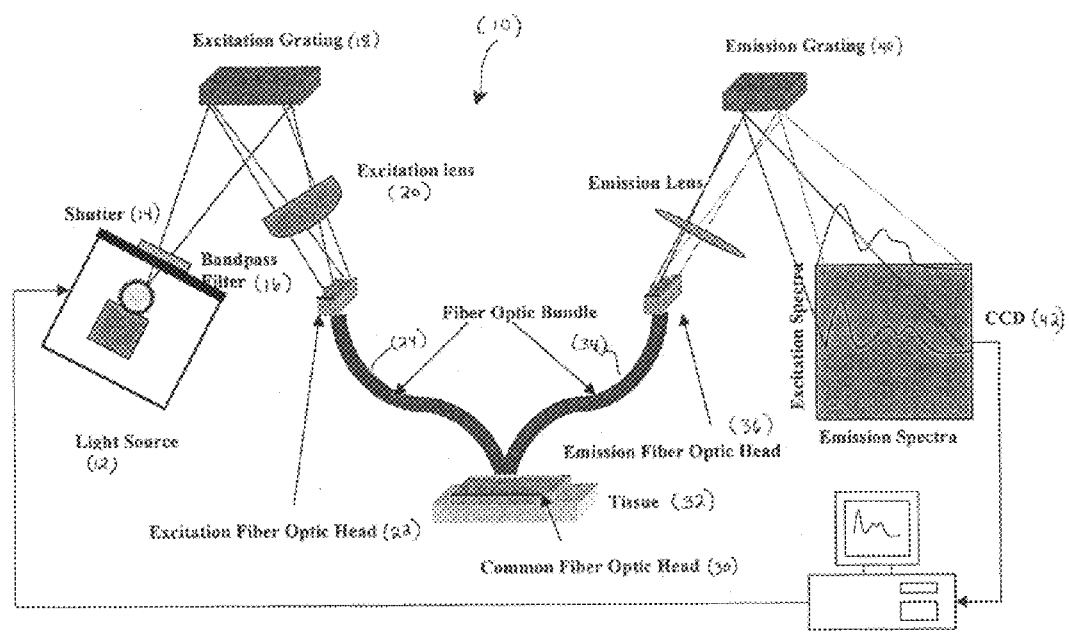
FIG. 1 A schematic of an instrument of a preferred embodiment of the invention.
Figure 2:
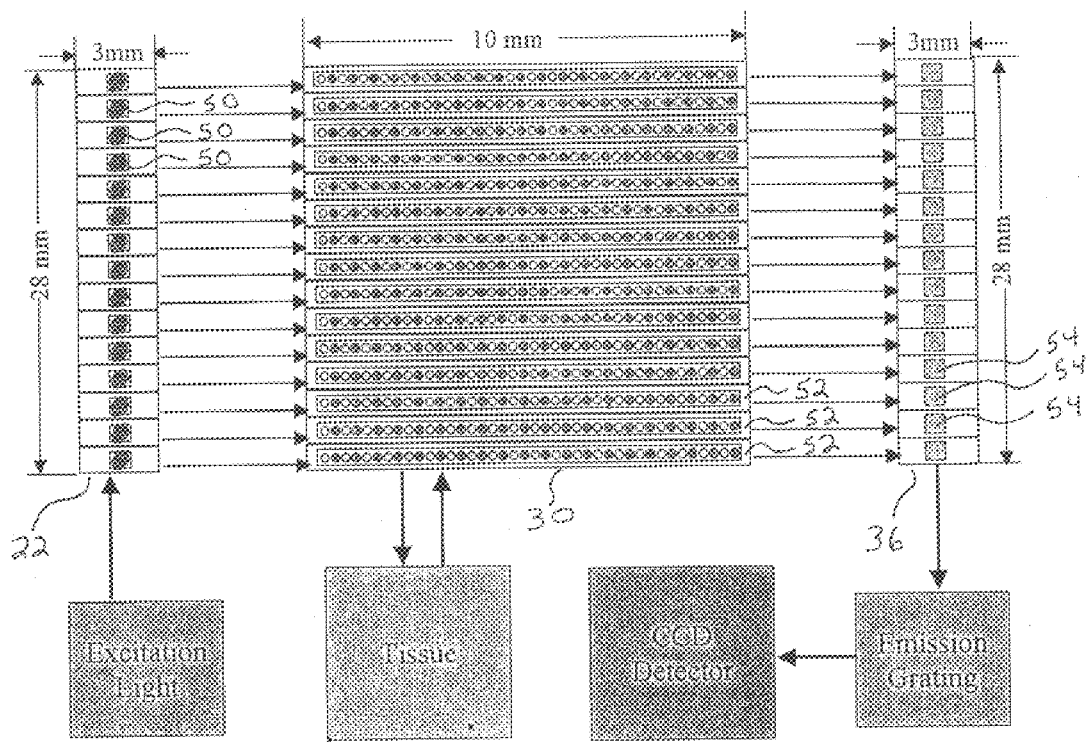
FIG. 2 A schematic of the fiber optic heads of the instrument of FIG. 1.

A preferred embodiment of an instrument according to the invention is diagrammed in FIG. 1, and the fiber optic heads of the instrument are shown in more detail in FIG. 2.

Referring to FIG. 1, three-dimensional fluorescence spectrometer 10 comprises a light source 12. Light source 12 is preferably a UV-visible light source. Light source 12 may be a continuous source with a shutter 14 or, more preferably, a flash lamp. Excitation radiation at a plurality of excitation wavelengths from light source 12 passes through bandpass filter 16 where it strikes excitation grating 18. From excitation grating 18, the excitation radiation is directed through excitation lens 20 to excitation optical fiber head 22. As will be clear to those of skill in the art, the excitation optics spectrally disperse the incident radiation and lead it to the excitation optical fiber head 22.

Excitation radiation then passes from excitation optical fiber head 22 via fiber optic bundle 24 to common fiber optic head 30. Excitation radiation from excitation fibers in common fiber optic head 30 is directed to the tissue or surface of interest 32.

Fluorescent radiation emitted from the tissue is then picked up by emission fibers in common fiber optic head 30. The collected emission radiation is transmitted via emission fiber optic bundle 34 to emission fiber optic head 36. From emission fiber optic head 36, the collected radiation passes through emission lens 38 to the emission optics, i.e., emission grating 40. From emission grating 40, the collected radiation is sent to a two-dimensional CCD detector or similar photon detector 42.

The emission radiation is collected by a two-dimensional array of detector elements disposed in common fiber optic head 30. The two-dimensional detector disposition is arranged by wavelength to form a two-dimensional excitation-emission map in which all elements in the map are collected at once. Both the excitation and emission maps are gathered simultaneously using two-dimensional CCD 42. Spatial averaging of the excitation and emission radiation is then used to ameliorate any problems due to inhomogeneity.

FIG. 2 depicts a detailed schematic of excitation fiber optic head 22, common fiber optic head 30 and emission fiber optic head 36 according to a preferred embodiment of the invention. Referring to FIG. 2, excitation fiber optic head 22 preferably measures 28×3 mm and comprises 15 fiber bundles 50, each fiber bundle containing 20 fibers.

Common fiber optic head 30 preferably measures 28×10 mm and comprises 15 linear mixed fiber arrays 52 from the excitation and emission bundles. Preferably, each linear array 52 contains 40 fibers, 20 excitation fibers and 20 emission fibers.

Emission fiber optic head 36 preferably measures 28×3 mm and comprises 15 fiber bundles 54.

At the excitation end, each fiber bundle 50 preferably contains 20 optic fibers of 0.2 mm diameter, and collects narrowband light (bandwidth 8–20 nm) in a selected UV and visible wavelength region. The excitation wavelengths are preferably 250–550 nm, more preferably, 270–450 nm, and most preferably, 270–390 nm. There is 0.8 mm space between each fiber bundle to mitigate cross-talk. Thus, in the preferred embodiment, there are 300 fibers in each bundle.

The emission fibers are also arranged in 15 fiber bundles 54 comprising 20 fibers each at the emission end of the fiber bundle, arranged as the emission fibers.

At the common end, each linear fiber array 52 (10 mm long, containing 20 each of alternating excitation and emission fibers) delivers narrowband excitation light to a 10 mm strip of tissue. Different strips excite the tissue at different wavelengths and collect the fluorescence.

The arrangement depicted in FIG. 2 provides the following advantages:

1. The relatively large area of common head reduces the problem of inhomogeneity of tissue site by spatially averaging.
2. By using a 2-dimensional CCD array, the need for a moving detector system is eliminated. This speeds up collection as well as simplifies the design.
3. By collecting the spectra in parallel, rather than sequentially, UV exposure on the tissue is minimized.

Other embodiments and uses of the invention will be apparent to those skilled in the art from consideration of the specification and practice of the invention disclosed herein. All references cited herein, including all U.S. and foreign patents and patent applications, are specifically and entirely hereby incorporated herein by reference, including, but not limited to: U.S. patent application Ser. No. 09/287,486, filed Apr. 6, 1999, titled "Non-invasive Tissue Glucose Level Monitoring," issued Jan. 7, 2003 as U.S. Pat. No. 6,505,059; U.S. patent application Ser. No. 09/785,531, titled "Multivariate Analysis of Green to Ultraviolet Spectra of Cell and Tissue Samples;" U.S. patent application Ser. No. 09/785,559, titled "Reduction of Inter-Subject Variation Via Transfer Standardization;" and U.S. patent application Ser. No. 09/785,547 titled "Non-Invasive Tissue Glucose Level Monitoring," all filed contemporaneously herewith. It is intended that the specification and examples be considered exemplary only, with the true scope and spirit of the invention indicated by the following claims.

What is claimed is:

1. A common fiber optic head, comprising:
   a plurality of excitation fiber optic bundles, wherein each of the plurality of excitation fiber optic bundles comprises at least twenty excitation fibers;
   a plurality of emission fiber optic bundles, wherein each of the plurality of emission fiber optic bundles comprises at least twenty emission fibers; and wherein distal ends of the excitation and emission fiber optic bundles are disposed in a two-dimensional array.

2. The common fiber optic head of claim 1, wherein the two-dimensional array comprises n rows and n columns;

the distal ends of the excitation fiber optic bundles are disposed in all elements of every odd or even column, but not both; and wherein the distal ends of the emission fiber optic bundles are disposed in all elements of every odd or even column not occupied by the excitation fiber optic bundles.

3. The common fiber optic head of claim 2, wherein each of the excitation fibers carries excitation light having a wavelength between 250–550 nm.

4. The common fiber optic head of claim 3, wherein each column of the excitation fibers carries excitation light having a unique wavelength.

5. The common fiber optic head of claim 1, wherein the excitation and emission fiber optic bundles are spaced at least 0.5 mm apart.

6. The common fiber optic head of claim 1, wherein the emission fibers collect fluorescence emitted from a sample.

7. A system comprising:

a common fiber optic head, an excitation radiation source, and an emission radiation detector, wherein the common fiber optic head further comprises a plurality of excitation fiber optic bundles each of which comprises at least twenty excitation fibers; a plurality of emission fiber optic bundles each which comprises at least twenty emission fibers; and wherein distal ends of the excitation and emission fiber optic bundles are disposed in a two-dimensional array.

8. The system of claim 7, further comprising means for generating a two-dimensional excitation and emission radiation map in which all elements in the map are gathered at once.

* * * * *